United States Patent [19]

Klun et al.

[11] Patent Number: 4,480,121

[45] Date of Patent: Oct. 30, 1984

[54] PREPARATION OF 2-HALO-1-ALKENES AND ACRYLATE ESTERS FROM HYDROCARBON STREAMS

[75] Inventors: Robert T. Klun; Craig B. Murchison; Dennis A. Hucul, all of Midland, Mich.

[73] Assignee: The Dow Chemical Company, Midland, Mich.

[21] Appl. No.: 411,726

[22] Filed: Aug. 26, 1982

[51] Int. Cl.$^3$ .................... C07C 67/36; C07C 17/08
[52] U.S. Cl. .................... 560/206; 560/104; 560/114; 560/207; 560/130; 570/231; 570/232
[58] Field of Search ............... 570/165, 169, 231, 232, 570/182, 186; 560/206, 207, 104, 114, 130

[56] References Cited

U.S. PATENT DOCUMENTS

| | | | |
|---|---|---|---|
| 3,142,710 | 7/1964 | Arganbright | 570/232 |
| 3,377,389 | 4/1968 | Griesbaum | 570/186 |
| 3,413,364 | 11/1968 | Blumenthal | 570/231 |
| 3,457,299 | 7/1969 | Closson et al. | 560/207 |
| 3,465,053 | 9/1969 | Sennewald et al. | 570/232 |
| 3,626,005 | 12/1971 | Scheben et al. | 560/207 |
| 3,988,358 | 10/1976 | Heck | 560/207 |
| 3,991,101 | 11/1976 | Knifton | 560/207 |
| 4,061,724 | 12/1977 | Grose et al. | 423/335 |

FOREIGN PATENT DOCUMENTS

| | | |
|---|---|---|
| 0031200 | 7/1981 | European Pat. Off. . |
| 1505099 | 12/1965 | France . |
| 47-25050 | 7/1972 | Japan . |
| 2034291 | 8/1978 | United Kingdom . |

OTHER PUBLICATIONS

Kovachic, D. et al., *Can. J. Chem.* vol. 39, (1961) pp. 363–374.
Griesbaum, Karl et al., *J. Org. Chem.* vol. 29, (1964) pp. 2404–2408.
Charleston, Barbara S. et al., *Tetrahedron Letters* (1969) pp. 5147–5150.
Amar, Francois et al. *Tetrahedron Letters* (1974) pp. 3037–3042.
Herbertz, Theo, *Chemische Berichte* vol. 92, (1959) pp. 540–550.
Griesbaum, Karl et al., *Chemische Berichte* vol. 106, (1973) pp. 2001–2008.
Holleman, A. F., "*A Textbook of Inorganic Chemistry*" (1916) 5th Ed., John Wiley, Publ., pp. 39 & 40.

*Primary Examiner*—Natalie Trousof
*Assistant Examiner*—L. Hendriksen
*Attorney, Agent, or Firm*—Norman L. Sims

[57] ABSTRACT

The invention is a process for preparing a 2-halo-1-alkene comprising contacting a hydrocarbon stream with a hydrogen halide, in the presence of water and an effective amount of a catalyst, at a temperature between about 20° C. and about 400° C., wherein; the hydrocarbon stream comprises a 1,2-diene, a terminal acetylene or mixtures thereof, represented by the formulas $CH_2=C=CH-R$ or $CH\equiv C-CH_2-R$ wherein R is hydrogen, alkyl, cycloalkyl or aryl and may be substituted or unsubstituted; the water is present in an amount capable of maintaining the selectivity of the catalyst for the insertion of the halide on the 2 carbon of the 1,2-diene or terminal acetylene; and the catalyst comprises carbon, silica alumina, aluminosilicates, silica gel, silica, silica magnesia, silicalite, group IIIA, IIIB, IVA, IVB or V metal oxides or rare earth oxides.

The invention further includes the additional step of preparing an acrylate ester by contacting the 2-halo-1-alkene, with carbon monoxide and an esterifying agent such as an alcohol, phenol, carbonate, or (poly)glycol monoether, in the presence of a group VIII metal catalyst and a halogen acceptor.

14 Claims, No Drawings

PREPARATION OF 2-HALO-1-ALKENES AND ACRYLATE ESTERS FROM HYDROCARBON STREAMS

BACKGROUND OF THE INVENTION

The invention relates to an improved process for the preparation of 2-halo-1-alkenes from light hydrocarbon streams. It further relates to a process for preparing acrylate esters from the 2-halo-1-alkenes.

Griesbaum, U.S. Pat. No. 3,377,389, Apr. 9, 1968, teaches that hydrogen chloride and hydrogen bromide will add to unsaturated compounds in accordance with Markovnikov's Rule and that allene (propadiene) and methylacetylene (propyne) are hydrohalogenated to give 2-halopropene.

Kovachic and L. C. Leitch, "Organic Deuterium Compounds", Can. J. Chem., 39, 363–374 (1961) teach that 2-halo-1-alkenes can be prepared by addition of hydrogen chloride to 1-alkynes. It is taught this addition can be performed in the presence of dibenzoyl peroxide or under ultraviolet illumination.

Arganbright, U.S. Pat. No. 3,142,710, teaches that propyne and propadiene can be selectively halogenated in the presence of propylene. Propylene containing minor amounts of propyne and propadiene together with hydrogen chloride are passed over a catalyst comprising mercuric halide deposited on a porous carrier, particularly one having high surface activity at a temperature in the range of from about 100° C. to about 120° C.

Schroeder and Slewka, French Patent No. 1,505,099 (Dec. 18, 1965), teach that a $C_3$ hydrocarbon stream may be purified by selectively removing propadiene (allene) and propyne (methyl acetylene) by reacting the $C_3$ hydrocarbon stream with hydrogen chloride in the presence of hydrochlorination catalysts, in particular mercuric chloride on a support such as activated aluminum oxide, silica gel or activated carbon. The propadiene and propyne are selectively halogenated to prepare 2-chloropropene which is easily separated from the other components of the $C_3$ light hydrocarbon stream.

Herbertz, "Von Aliphatischen Acetylenkohlenwasserstoffen ausgehende Synthesen", Chem. Ber., 92, 540–50 (1959), teaches two processes for the addition of hydrogen halides to alkynes. One is a mixed phase reaction wherein copper (I)-chloride is the catalyst. In the other, the alkyne is vaporized and mixed with hydrogen chloride and passed over activated charcoal in the presence of mercury at a temperature of 130° C.

A process for selectively halogenating a 1,2-diene and a terminal acetylene with a hydrogen halide in the presence of other hydrocarbons wherein the yields of the 2-haloalkenes are substantially higher than prior art processes permit has been discovered.

The 2-halo-1-alkenes prepared by this process can be carbonylated and esterified to prepare acrylate esters if desired.

One such acrylate ester is methyl methacrylate which is prepared commercially from acetone which is treated with HCN to give 2-cyano-2-propanol which is then treated with 98 percent sulfuric acid to give a salt of propene-2-amide and sulfuric acid. The salt is then reacted with methanol to prepare methyl methacrylate and $NH_4HSO_4$. This process requires a large purification scheme and the use of sulfuric acid and hydrogen cyanide.

It is desirable to prepare methacrylates without the use of sulfuric acid and hydrogen cyanide.

SUMMARY OF THE INVENTION

The invention is a process for preparing a 2-halo-1-alkene comprising contacting a hydrocarbon stream with a hydrogen halide, in the presence of water and an effective amount of a catalyst, at a temperature between about 20° C. and about 400° C., wherein; the hydrocarbon stream comprises a 1,2-diene, a terminal acetylene or mixtures thereof, represented by the formulas $CH_2=C=CH-R$ or $CH\equiv C-CH_2-R$ wherein R is hydrogen, alkyl, cycloalkyl or aryl and may be substituted or unsubstituted; the water is present in an amount capable of maintaining the selectivity of the catalyst for the insertion of the halide on the 2 carbon of the 1,2-diene or terminal acetylene; and the catalyst comprises carbon, silica alumina, aluminosilicates, silica gel, silica, silica magnesia, silicalite, group IIIA, IIIB, IVA, IVB or V metal oxides or rare earth oxides.

The invention further includes the additional step of preparing an acrylate ester by contacting the 2-halo-1-alkene, with carbon monoxide and an esterifying agent such as an alcohol, phenol, carbonate, or (poly)glycol monoether, in the presence of a group VIII metal catalyst and a halogen acceptor.

The acrylate esters produced by this process are useful as monomers in the preparation of polymers which have use in preparing latexes and molded or cast articles including sheets and panels for glazing or other uses.

DETAILED DESCRIPTION OF THE INVENTION

In this invention, a hydrocarbon stream comprising a 1,2-diene, a terminal acetylene or mixtures thereof, is reacted with a hydrogen halide to prepare a 2-halo-1-alkene. This can be represented by the following equations:

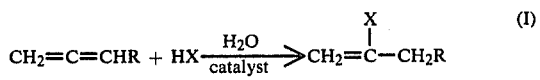

or

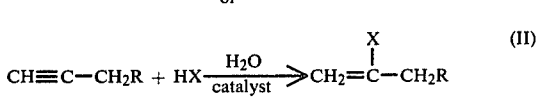

wherein X is chlorine, bromine, iodine or fluorine; and wherein R is hydrogen, alkyl, cycloalkyl or aryl and may be substituted or unsubstituted. The 2-halo-1-alkene can be separated from the unreacted hydrocarbons, hydrogen halide and any by-products by conventional means, such as distillation.

The hydrocarbon streams as used herein can contain saturated alkanes, alkenes, dienes and alkynes. A $C_3$ hydrocarbon stream as used herein can contain propane, propylene, propadiene and propynes with minor amounts of $C_2$, $C_4$ and $C_5$ aliphatic compounds. In such streams, the active species are the 1,2-dienes and the terminal acetylenes.

The hydrocarbon stream which is halogenated preferably comprises a 1,2-diene of equation I, terminal acetylene of equation II or mixtures thereof (hereinafter referred to as active species) wherein R is lower alkyl or hydrogen. More preferably, R is hydrogen, the 1,2-diene is propadiene and the terminal acetylene is propyne. In this more preferred embodiment, any hydrocarbon stream containing propadiene, propyne or a mixture thereof can be used. A hydrocarbon stream consisting essentially of propadiene and propyne can be used, but it is preferable that the hydrocarbon stream have less than 65 percent of these active compounds as above this concentration, such a stream is explosive. A hydrocarbon stream of $C_3$ compounds including the active species is a good starting stream.

2-Halopropene is produced where the hydrocarbon stream is a $C_3$ stream containing propadiene, propyne or mixtures thereof.

The hydrogen halide can be hydrogen bromide, hydrogen chloride, hydrogen iodide or hydrogen fluoride. Hydrogen chloride and hydrogen bromide are preferred.

The halogenation of the active species in the hydrocarbon stream can be done in either the liquid phase or the vapor phase. The vapor phase is preferred because in the liquid phase higher concentrations of the active species may be present increasing the risk of explosion. In the liquid phase, the halogenation may be run with or without a catalyst.

Surprisingly, suitable catalysts include carbon, silica alumina, silica gel, silica magnesia, silicalite, aluminosilicates, group IIIA, IIIB, IVA, IVB or V metal oxides or rare earth oxides. The catalysts may be impregnated with mercuric halide or barium bromide as is taught in U.S. Pat. No. 3,142,710, but contrary to the teachings in the patent, such compounds are not necessary to catalyze this reaction. Preferred catalysts are carbon and alumina. The most preferred catalyst is alumina. The catalyst has a significant effect on the selectivity of the insertion of the halogen on the unsaturated active species in the hydrocarbon stream. Those aluminas with high surface area, high acidity and with low silica content demonstrate the best activity.

These catalysts can be regenerated by passing water saturated air through the catalyst for a period of several hours at elevated temperatures.

It has been discovered that the presence of water in the halogenation of the active unsaturated hydrocarbons maintains the selectivity of the catalyst during prolonged use. After a short period, four or five hours, the selectivity of the catalyst drops significantly in the absence of water. The use of water during the process maintains the selectivity of the catalyst over the catalyst lifetime. It is believed the addition of the water to the process maintains the surface hydroxyls on the catalyst.

A relatively small amount of water is necessary. That amount of water which is capable of maintaining the selectivity of the catalyst for the insertion of the halide on the 2 carbon of the 1,2-diene or terminal acetylene is sufficient. In practice, this may be achieved by saturating the hydrocarbon stream with water vapor prior to contacting it with the hydrogen halide and the catalyst.

The hydrogen halide can be added in any ratio to the active unsaturated compounds in the hydrocarbon stream. A suitable molar ratio is between about 0.7 and 1.5 moles of hydrogen halide per mole of active species. The use of excess hydrogen halide may result in the halogenation of compounds in the hydrocarbon stream other than the active unsaturated species and the preparation of 1,2-dihaloalkanes from the active species.

This process can be run at temperatures between $-78°$ C. and 400° C. It has been discovered that a preferable temperature range is between about 100° C. and 300° C. Below 100° C. selectivity is reduced and above 300° C. little improvement in selectivity is found. Most preferably the temperature is between about 200° C. and 300° C. as selectivity is at its optimum in this range. In the vapor phase process where the streams of reactants are passed over the catalyst it is desirable to preheat the streams to the reaction temperature prior to passing them over the catalyst.

This step may be run at atmospheric or superatmospheric pressure. It is believed that superatmospheric pressures would improve the rate of reaction.

The 2-halo-1-alkenes prepared by the invented process can be isolated by conventional means and carbonylated and esterified to prepare an acrylate ester. This may be done in either the vapor or the liquid phase. Acrylate esters represented by the formula below may be prepared by this process:

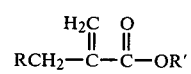

wherein

R is hydrogen, alkyl, cycloalkyl or aryl and may be substituted; and

R' is aryl, alkyl, cycloalkyl or benzyl and may be substituted.

The 2-halo-1-alkene is carbonylated and esterified by contacting it with an esterifying agent and carbon monoxide, in the presence of a group VIII metal catalyst and a halogen acceptor to prepare the acrylate ester. The reaction wherein R'OH is the esterifying agent, can be represented by the following equation (III):

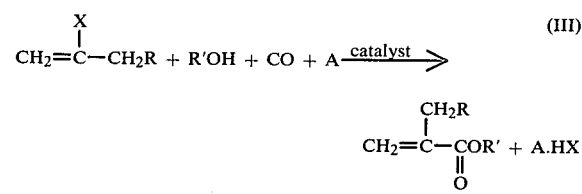

wherein R' is aryl, alkyl, cycloalkyl or benzyl and may be substituted with an alkyl, aryl, cycloalkyl, nitro, cyano, ester, carboxylate, amide, aldehyde, hydroxyl, amino, substituted amino or halogen, if these groups are less reactive than the other groups in the reactants which are intended to take part in the reaction; A is a halogen acceptor which will be defined below; and X and R are as previously defined.

The acrylate ester produced is separated from any unreacted materials, the catalyst, the halogen acceptor and any solvent used, by any suitable process, such as distillation.

The esterifying agent (R'OH) used in the esterification of the 2-halo-1-alkene may be any alcohol or phenol that has a reactive hydroxyl group. Alcohols and phenols with 1 to 20 carbon atoms or more may be employed. Examples of such alcohols and phenols include paraffinic alcohols and cycloparaffinic alcohols; such as methanol, ethanol, propanol, phenol, cresol, xylenol, naphthol, cyclopentanol and cyclohexanol. Polyols, such as diols and triols may also be used, for example, ethylene glycol and glycerol.

The order of reactivity of alcohols from most to least is primary, secondary and tertiary. R' is preferably a $C_{1-10}$ lower alkyl and substituted or unsubstituted phenol, more preferably R' is a $C_{1-10}$ lower alkyl and most preferably R' is a methyl group.

Carbonates of the formula

and (poly)glycol monoethers of the formula

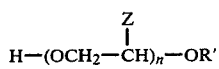

wherein R' is as defined above; n is an integer from 1 to 10; and Z can be, separately in each occurrence, hydrogen or methyl, can also be reacted with the 2-halo-1-alkene to prepare the α-acrylate esters. R' is preferably a $C_{1-10}$ lower alkyl and most preferably a methyl group.

A halogen acceptor is used in this step to prevent the formation of free hydrogen halide or to reduce any hydrogen halide formed. The presence of a free hydrogen halide in the reaction can create problems because of its corrosive nature and inhibition of the reaction.

The halogen acceptor can be an excess of the compound used to esterify the 2-halo-1-alkene, that is an alcohol, phenol, organic carbonate, or (poly)glycol monoether. Where an alcohol or phenol is used the halogen reacts to form a halogenated hydrocarbon, and the hydroxyl group on the alcohol accepts the free hydrogen ions to form water. For example, where methanol is used as a halogen acceptor, methyl halide and water are formed.

An amine can be added to the reaction to function as a halogen acceptor. Suitable amines are represented by the formula $(R^2)_3N$ wherein $R^2$ is separately in each occurrence, hydrogen alkyl, cycloalkyl or aryl. Optionally two of the $R^2$ groups may together form an alkylene group. Polyvinyl pyridine resins have also been found to be suitable halogen acceptors. Tertiary amines are preferable amine halogen acceptors as primary and secondary amines will react with the carbonylated alkene intermediate to form an amide. Preferably $R^2$ is a lower alkyl group. Examples of tertiary amines which can be used include triethylamine, tri-n-propylamine, tri-n-hexylamine, tri-n-butylamine, tri-n-octylamine, triisopropylamine, tetramethylene diamines, N-methyl piperidine, N,N-dicyclohexylethylamine, benzyldiethylamine, dimethylisopropylamine, quinoline, 2,4,6-trimethylpyridine, pyridine, N,N-dimethylbenzylamine, 2-methyl pyridine, N,N-dimethylamine toluide.

When an amine is used as a halogen acceptor, an amine hydrogen halide salt is formed.

Inorganic compounds may also be used as halogen acceptors. Suitable inorganic halogen acceptors include calcium oxide, zinc oxide, sodium carbonate, potassium hydroxide and the like.

A portion of the hydrocarbon stream used in this process can also be used as a halide acceptor. In this embodiment of the invention, the hydrocarbons are added to the reaction and the unsaturated active species reacts with the hydrogen halide formed in the esterification of the 2-halo-1-alkene to form more 2-halo-1-alkene, which can then be carbonylated and esterified to the acrylate ester.

Carbon monoxide is added to the reaction by pressurizing the reaction vessel or zone with carbon monoxide gas and maintaining positive pressure with carbon monoxide gas throughout the process. Carbon monoxide can be present in an excess amount. Use of excess carbon monoxide can increase yields. It is desirable to employ from about 1.0 to about 25 or more moles of carbon monoxide per each mole of 2-halo-1-alkene. A preferred amount is from about 1 to about 15 moles.

The esterifying compound used to esterify the 2-halo-1-alkene should be present in a molar ratio of the former to the latter of 1:1. If the esterifying compound is used as a halogen acceptor, a molar ratio of 2:1 or greater is preferred.

Where the halogen acceptor is an amine, at least one mole of amine for each mole of hydrogen halide produced should be added to the reaction.

The catalyst is some form of a group VIII metal. Preferred group VIII metals are palladium, cobalt, rhodium, iridium, nickel or platinum, with palladium most preferred. The metals can be employed either as homogeneous or heterogeneous catalysts. Homogeneous catalysts are preferred when the reaction is run in the liquid phase.

When the group VIII metals are employed as heterogeneous catalysts, either the metal or a salt of the metal is supported on an inert carrier of activated carbon, silica alumina, silica gel, silicalite, activated clays, ion-exchange resins, or titanium, zirconium, magnesium, aluminum or silicon, or oxides thereof. Alumina supports are preferred.

These supported catalysts can be prepared by conventional means, well-known to the art. The palladium on support shows better catalytic activity where the catalyst is prepared from palladium chloride salt. Reduction temperatures between about 230° C. and 300° C., are preferred and give a more active catalyst.

Where palladium is used as the catalyst, between about 0.1 and 10 percent by weight of the support of palladium can be used, preferably between about 0.1 and 2.0 percent by weight of the support.

The reaction temperature is between about 150° C. and 300° C. for a heterogeneous catalyst, preferably between about 220° C. and 250° C. Pressure should be between about 100 and 5000 psi, preferably between about 400 and 1000 psi.

The group VIII metal can also be used in a homogeneous catalyst. In this form the metal is used in a complex in which the metal can be reduced to the zero valence state, as it is believed that the catalytic species of these metals are the zero valent species. The complex can be represented by the formula $Y_mB(LR_3'')_p$ wherein B is a group VIII metal; Y is chlorine, bromine, iodine, fluorine, acetate or $NO_3$ and the like; L is nitrogen, phosphorus or arsenic; m is an integer between 0 and 2; p is an integer between 0 and 4; and R'' is separately in each occurrence, alkyl, aryl, alkoxy, aryloxy, thioalkyl, thioaryl or acetate.

L is preferably phosphorus; R is preferably alkyl, aryl or acetate; and B is preferably palladium, cobalt, rhodium, iridium, nickel or platinum and most preferably palladium. Both m and p are preferably 2.

These complexes may be prepared in situ, or prior to being added to the reaction. When palladium is used, between about 0.01 and 10 mole percent can be used, between about 0.1 and 1.0 mole percent is preferred.

The temperature for this reaction with a homogeneous catalyst is between about 50° C. and 200° C., preferably 100° C. and 160° C. Below 50° C., the reaction rate is too low, at 160° C. the catalyst begins to decompose.

The preferred method of carbonylation and esterification of a 2-bromo-1-alkene is a liquid phase reaction with a homogeneous catalyst.

The presence of oxygen can be detrimental to this reaction.

The carbonylation and esterification step may be run in the presence of a solvent. The solvent can be an excess of the alcohol, carbonate, (poly)glycol, (poly)glycol monoether or tertiary amines, which are present either to esterify the carbonylated 2-halo-1-alkene, or present as a halogen acceptor. Alternatively, this step may be carried out in the presence of an inert solvent such as a hydrocarbon or a (poly)glycol diether. The hydrocarbons employed can be either aliphatic, alicyclic or aromatic. Suitable solvents include cyclohexane, benzene, toluene, isooctane, xylene, mesitylene, ether, kerosene, No. 9 oil, 1,3,5-hexanetriether and (poly)alkylene glycol diethers. Of the above-described solvents, those with a boiling point above 160° C. are preferred for use with a homogeneous catalyst as such catalysts decompose above 160° C. Ethylene glycol dimethyl ether is a preferred solvent for use with the homogeneous catalyst.

In one embodiment where the 2-halo-1-alkene is 2-chloropropene or 2-bromopropene and the alcohol is methanol, the acrylate ester prepared is methyl methacrylate.

The process disclosed herein can further include a step wherein the halogen acceptor which has accepted a halogen or a hydrogen halide is removed from the reactor and decomposed or dissociated to release the hydrogen halide and the residual organic compound.

Organic halides, such as methyl bromide, are by-products of the reaction in the carbonylation and esterification where an alcohol, phenol, carbonate or (poly)glycol monoether is used as the halogen acceptor. The organic halide may itself be commercially valuable. It can also be decomposed to hydrogen halide and the residual organic compound by reacting the organic halide with hydrogen at a temperature of between about 300° C. and 600° C. in the presence of a suitable catalyst. Suitable catalysts are oxides of chromium, vanadium, tungsten, cerium, molybdenum or aluminum molecular sieves. This process is disclosed and taught in Davis, U.S. Pat. No. 3,875,293 (incorporated herein by reference). The hydrogen halide recovered by this process can be used to halogenate the active species in the hydrocarbon stream.

An amine hydrohalide is a by-product of the carbonylation and esterification step when an amine is used as a halogen acceptor. This salt can be decomposed to an amine and the hydrogen halide by thermal cleavage. The thermal cleavage process is taught in Coenen et al., British Patent No. 2,034,291 (incorporated herein by reference). The hydrogen halide recovered by this process can be used to halogenate the active species in the hydrocarbon stream.

SPECIFIC EMBODIMENTS

Having generally described the invention, a more complete understanding can be obtained by reference to certain specific examples, tests and experiments which are included for purposes of illustration and are not intended to limit the scope of the claims.

EXAMPLE 1

Hydrobromination of a Crude $C_3$ Stream Using Alumina

Through a tube reactor, heated to 215° C. at atmospheric pressure and loaded with 15 cc of alumina plus inert quartz chips packing, was passed 27.5 ml/min of HBr gas and 90.0 ml/min of a crude $C_3$ stream saturated with water vapor. The molar composition of the $C_3$ stream was 16.8 percent propadiene, 22.8 percent propyne, 52.4 percent propylene, 6.5 percent propane and 1.5 percent mixed $C_4$ hydrocarbons. Approximately 65 percent total propyne and propadiene conversion was achieved with about 95 percent selectivity to 2-bromopropene.

EXAMPLE 2

Hydrochlorination of a Crude $C_3$ Stream Using Alumina

Through a tube reactor, heated to 290° C. at atmospheric pressure and loaded with 50 cc of alumina plus inert quartz chips packing, was passed 73.0 ml/min of HCl gas and 150 ml/min of a crude $C_3$ stream saturated with water vapor. The molar composition of the $C_3$ stream was 24.0 percent propadiene, 27.2 percent propyne, 18.8 percent propylene, 23.4 percent propane and 6.6 percent mixed $C_4$ hydrocarbons. Approximately 73 percent total propyne and propadiene conversion was achieved with approximately 98 percent selectivity to 2-chloropropene.

EXAMPLES 3–10

Examples 3–10 were run in a manner similar to Examples 1 and 2. The results are compiled in Table I. In Table I, actives conversion refers to the percentage of propyne and propadiene which was halogenated and selectivity refers to the percentage of the 2-halopropene in such halogenated compounds.

Table I demonstrates that alumina is the best catalyst for step (a). Further, Examples 1–3 demonstrate that the presence of water increases the selectivity of the reaction for 2-halopropene.

Table II shows the composition of the $C_3$ stream of Examples 3 to 10.

TABLE I

| Example No. | Hydrogen Halide | Catalyst | Temp °C. | Water Vapor | HX flow rate | $C_3$ Stream flow rate ml/min | Conversion % | Selectivity % |
| --- | --- | --- | --- | --- | --- | --- | --- | --- |
| 1 | HBr | Alumina | 215 | yes | 27.5 | 90.0 | 65 | 95 |
| 2 | HCl | Alumina | 290 | yes | 73.0 | 150.0 | 73 | 98 |
| 3 | HBr | Alumina | 220 | no | 19.0 | 106.0 | 65 | 90 |
| 4 | HBr | Carbon impregnated with 28% BaBr and 0.7% HgBr | 215 | no | 35.5 | 120.0 | 70 | 84 |
| 5 | HBr | Zirconia | 265 | no | 27.5 | 90.0 | 42 | 73 |
| 6 | HBr | Silica Alumina | 240 | no | 36.0 | 100.0 | 30 | 53 |
| 7 | HBr | Silicalite | 222 | no | 36.0 | 100.0 | 15 | 28 |

TABLE I-continued

| Example No. | Hydrogen Halide | Catalyst | Temp °C. | Water Vapor | HX flow rate | C3 Stream flow rate ml/min | Conversion % | Selectivity % |
|---|---|---|---|---|---|---|---|---|
| 8 | HBr | Titania | 275 | no | 31.0 | 103.0 | 41 | 79 |
| 9 | HBr | Magnesia | 212 | no | 28.0 | — | 5 | 38 |
| 10 | HBr | Carbon | 265 | yes | 25.0 | 96.0 | 60 | 83 |

TABLE II

Composition of C3 Streams Examples 3–10

| Example | Propa-diene | Pro-pyne | Pro-pylene | Pro-pane | C4 Hydro-carbons |
|---|---|---|---|---|---|
| 3 | 11.7 | 14.4 | 46.6 | 27.0 | 0.4 |
| 4 and 10 | 16.4 | 20.6 | 54.6 | 6.8 | 1.5 |
| 5–9 | 16.8 | 22.8 | 52.4 | 6.5 | 1.5 |

EXAMPLE 11

Preparation of Methyl Methacrylate with Dichlorobis(triphenylphosphine)Palladium Catalyst from 2-Chloropropene To a stirred high pressure reactor was added 26.42 g of tri-n-butylamine, 1.3 g of dichlorobis(triphenylphosphine)palladium catalyst, 5.1 g of methanol and 9.9 g of chloropropene. The reactor was pressurized to 300 psig with carbon monoxide, heated to 110° C. and stirred for 20 hours. Analysis of the product mixture showed methyl methacrylate and unreacted chloropropene to be present.

EXAMPLE 12

Preparation of Methyl Methacrylate from 2-Bromopropene with Dichlorobis(triphenylphosphine)palladium Catalyst To a stirred high pressure reactor was added 30.82 g of tri-n-butylamine, 1.54 g of dichlorobis(triphenylphosphine)palladium catalyst, 5.92 g of methanol and 18.15 g of 2-bromopropene. The reactor was pressurized to 300 psig with carbon monoxide, heated to 100° C. and stirred for 1.5 hours. Analysis showed complete consumption of 2-bromopropene starting material with methyl methacrylate as the major product.

EXAMPLE 13

Preparation of Methyl Methacrylate from 2-Bromopropene with Palladium Diacetate Catalyst To a stirred high pressure reactor was added 60.0 g of tri-n-butylamine, 0.415 g of palladium diacetate, 5.10 g of methanol, 0.06 g of 2,4-dinitro-ortho-sec-butylphenol and 15.6 g of 2-bromopropene. The reactor was pressurized with carbon monoxide, heated to 160° C. and stirred for 15 minutes. Analysis showed methyl methacrylate as the major reaction product.

EXAMPLE 14

Preparation of Methyl Methacrylate from 2-Bromopropene with Dichlorobis(triphenylphosphine)palladium Catalyst To a stirred high pressure reactor was added 41.85 g of quinoline, 130.0 g of dichlorobis(triphenylphosphine)palladium catalyst, 0.06 g of 2,4-dinitro-ortho-sec-butylphenol and 5.10 g of methanol. The reactor was pressurized to 300 psig with carbon monoxide and heated to 110° C. Thereafter, 15.6 g of 2-bromopropene was added to the reaction mixture. After 0.5 hour, the reactor was cooled to room temperature. Analysis of the product mixture showed high conversion of the starting materials with methyl methacrylate as the major product.

EXAMPLE 15

Preparation of Methyl Methacrylate from 2-Bromopropene with Dichlorobis(triphenylphosphine)palladium Catalyst To a stirred high pressure reactor was added 39.26 g of 2,4,6-trimethyl pyridine, 1.30 g of dichlorobis(triphenylphosphine)palladium catalyst, 5.10 g of methanol and 0.06 g of 2,4-dinitro-ortho-sec-butylphenol. The reactor was pressurized to 300 psig with carbon monoxide and heated to 110° C. Then 15.6 g of 2-bromopropene was added to the reaction mixture. After 1 hour the reactor was cooled to room temperature. Analysis of the product mixture showed high conversion of starting materials with methyl methacrylate as the major product.

EXAMPLE 16

Preparation of Methyl Methacrylate from 2-Bromopropene with Dichlorobis(triphenylphosphine)palladium Catalyst A reaction the same as in Example 15 was run, except that 43.81 g of N,N-dimethylbenzylamine was used instead of 39.26 g of 2,4,6-trimethyl pyridine. After 0.75 hour the reactor was cooled to room temperature. Analysis of the product mixture showed high conversion of starting materials with methyl methacrylate as the major product.

EXAMPLE 17

Preparation of Methyl Methacrylate from 2-Bromopropene with Dichlorobis(triphenylphosphine)palladium Catalyst A reaction the same as in Example 15 was run, except that 30.17 g of α-picoline was used instead of 39.26 g of 2,4,6-trimethyl pyridine. After 0.75 hour the reactor was cooled to room temperature. Analysis of the product mixture showed high conversion of starting materials with methyl methacrylate as the major product.

EXAMPLE 18

Preparation of Methyl Methacrylate from 2-Bromopropene with Dichlorobis(triphenylphosphine)palladium Catalyst A reaction the same as in Example 15 was run, except that 43.8 g of N,N-dimethylaminetoluide was used instead of 39.26 g of 2,4,6-trimethyl pyridine. After 1 hour the reactor was cooled to room temperature. Analysis of the product mixture showed high conversion of starting materials with methyl methacrylate as the major product.

EXAMPLE 19

Preparation of Methyl Methacrylate from 2-Bromopropene and Dimethyl Carbonate with Dichlorobis(triphenylphosphine)palladium Catalyst To a stirred high pressure reactor was added 45.0 g of dimethyl carbonate, 0.05 g of dinitro-ortho-sec-butylphenol and 1.30 g of dichlorobis(triphenylphosphine)palladium. The reactor was pressurized to 300 psig with carbon monoxide and heated to 150° C. Then 12.1 g of 2-bromopropene was added to the reaction mixture. After 52 hours the reactor was cooled to room temperature. Analysis of the product mixture showed high conversion of starting materials with methyl methacrylate as the major product.

EXAMPLE 20

Preparation of Methyl Methacrylate from 2-Bromopropene with Dichlorobis(triphenylphosphine)palladium Catalyst To a stirred high pressure reactor was added 50.0 g of methanol, 0.05 g of dinitro-ortho-sec-butylphenol and 1.30 g of dichlorobis(triphenylphosphine)palladium. The reactor was pressurized to 300 psig with carbon monoxide and heated to 100° C. Then 12.1 g of 2-bromopropene was added to the reaction mixture. After 2.5 hours the reactor was cooled to room temperature. Analysis of the product mixture showed high conversion of starting materials with methyl methacrylate as the major product.

EXAMPLE 21

Preparation of Methyl Ether of Tetrapropylene Glycol Methacrylate from 2-Bromopropene with Dichlorobis(triphenylphosphine)palladium Catalyst To a stirred high pressure reactor was added 39.6 g of methyl ether of tetrapropylene glycol, 60.0 g of tri-n-butylamine, 0.06 g of dinitro-ortho-sec-butylphenol and 1.30 g of dichlorobis(triphenylphosphine)palladium. The reactor was pressurized to 300 psig with carbon monoxide and heated to 100° C. Then 15.6 g of 2-bromopropene was added to the reaction mixture. After 2 hours the reactor was cooled to room temperature. Analysis of the product mixture showed high conversion of starting materials with methyl ether of tetrapropylene glycol methacrylate as the major product.

EXAMPLE 22

Preparation of Methyl Methacrylate from 2-Chloropropene with a 1 Percent Palladium-on-Carbon Catalyst A mixture of 2-chloropropene and methanol, in a mole ratio of 2-chloropropene to methanol of 1:2, and carbon monoxide are passed over a fixed bed reactor containing 9.0 cc of a 1 percent palladium-on-carbon catalyst, at a flow rate of 25 cc/min and 7.2 cc/hour, respectively. The temperature was 235° C. and pressure 600 psig. Methyl methacrylate was produced at a rate of 0.05 g of methyl methacrylate per cubic centimeter of catalyst per hour.

EXAMPLE 23

Preparation of Methyl Methacrylate from 2-Bromopropene with a Palladium-on-Alumina Catalyst A mixture of 2-bromopropene and methanol, in a mole ratio of 1:2 respectively, and carbon monoxide are passed over a fixed bed reactor containing 15 cc of 0.3 percent palladium-on-alumina catalyst, at a rate of 20 cc/min and 7.2 cc/hour, respectively. At 210° C. and 600 psig the productivity of methyl methacrylate is 0.06 g of methyl methacrylate per cubic centimeter of catalyst per hour.

EXAMPLE 24

Effect of Temperature on the Selectivity of the Halogenation of a $C_3$ Hydrocarbon Stream to 2-Chloropropene A $C_3$ hydrocarbon stream containing propadiene and propyne and a stream of HCl were passed over an alumina catalyst for 98.5 hours. The $C_3$ stream was bubbled through water prior to passing over the catalyst. The temperature was gradually increased from 155.1° C. to 307.8° C. over the 98.5-hour period. Periodic samples were taken and analyzed. Table III shows the effect of temperature on the selectivity for 2-chloropropene of the chlorinated methyl acetylene and propadiene.

TABLE III

| Time (hours) | Temp. °C. | Selectivity (%) |
| --- | --- | --- |
| 6.00 | 155.6 | 50.8 |
| 9.25 | 177.6 | 71.5 |
| 13.75 | 198.0 | 84.8 |
| 17.50 | 216.0 | 92.1 |
| 31.25 | 231.0 | 93.9 |
| 52.30 | 231.0 | 91.1 |
| 63.00 | 251.7 | 98.2 |
| 77.45 | 271.1 | 98.5 |
| 86.00 | 331.1 | 98.8 |
| 92.25 | 307.8 | 97.5 |

This demonstrates that selectivity improves with an increase in temperature and that above 300° C. there is little improvement in selectivity.

EXAMPLE 25

Effect of Water Vapor on the Selectivity of the Halogenation of a $C_3$ Hydrocarbon Stream to 2-Bromopropene A $C_3$ hydrocarbon stream containing propadiene and propyne and a stream of HBr were passed over an alumina catalyst for 20.3 hours at a temperature ranging from 250° C. to 303° C. The hydrocarbon stream was bubbled through water prior to passing it over the catalyst. Table IV shows the selectivity over time.

TABLE IV

| Time (hours) | Selectivity for 2-Bromopropene (%) |
| --- | --- |
| 2.0 | 100.0 |
| 3.0 | 100.0 |
| 4.5 | 99.2 |
| 5.5 | 95.9 |
| 6.5 | 93.0 |
| 7.5 | 91.5 |
| 8.5 | 93.9 |
| 9.5 | 92.0 |
| 10.5 | 91.3 |

TABLE IV-continued

| Time (hours) | Selectivity for 2-Bromopropene (%) |
| --- | --- |
| 14.0 | 94.1 |
| 15.0 | 93.9 |
| 16.3 | 95.1 |
| 18.3 | 95.2 |
| 19.3 | 94.1 |
| 20.3 | 93.0 |

A $C_3$ hydrocarbon stream containing propadiene and propyne and a stream of HBr were passed over an alumina catalyst for 23.5 hours at a temperature ranging from 200° C. to 220° C. The $C_3$ stream was not bubbled through water. The selectivity over time is shown in Table V.

TABLE V

| Time (hours) | Selectivity for 2-Bromopropene (%) |
| --- | --- |
| 2.1 | 100.0 |
| 5.5 | 97.6 |
| 6.6 | 93.5 |
| 7.5 | 90.1 |
| 8.5 | 86.0 |
| 9.4 | 83.7 |
| 10.4 | 80.9 |
| 14.3 | 73.0 |
| 15.4 | 71.2 |
| 17.6 | 68.5 |
| 18.5 | 67.9 |
| 19.4 | 66.4 |
| 20.4 | 64.7 |

The above data demonstrates that the presence of a small amount of water kept the selectivity of the reaction for 2-bromopropene above 90 percent, whereas in the absence of the water, the selectivity of the reaction steadily decreased to 65 percent over the 20.3-hour period. This demonstrates that the presence of water has a significant effect in maintaining the selectivity for 2-bromopropene above 90 percent for a longer period of time.

What is claimed is:

1. A process for preparing a 2-halo-1-alkene comprising contacting a hydrocarbon stream with a hydrogen halide, in the presence of water and an effective amount of a catalyst, at a temperature between about 100° C. and about 400° C., wherein; the hydrocarbon stream comprises a 1,2-diene, a terminal acetylene or mixtures thereof, represented by the formulas $CH_2=C=CH-R$ or $CH\equiv C-CH_2-R$ wherein R is hydrogen, alkyl, cycloalkyl or aryl and may be substituted or unsubstituted; the water is present in an amount capable of maintaining the selectivity of the catalyst for the insertion of the halide on the 2 carbon of the 1,2-diene or terminal acetylene; and the catalyst comprises carbon, silica alumina, aluminosilicates, silica gel, silica, silica magnesia, silicalite, group IIIA, IIIB, IVA, IVB or V metal oxides or rare earth oxides.

2. The process of claim 1 wherein R is H or lower alkyl.

3. The process of claim 2 wherein the 1,2-diene is propadiene, the terminal acetylene is propyne and the 2-halo-1-alkene is 2-halopropene.

4. The process of claim 1 wherein the hydrocarbon stream is contacted with the hydrogen halide in the vapor phase.

5. The process of claim 1 wherein the catalyst is carbon or alumina.

6. The process of claim 1 wherein the temperature is between about 200° C. and 300° C.

7. The process of claim 1 wherein the hydrocarbon stream is saturated with water prior to contacting the stream with hydrogen halide and the catalyst.

8. The process of claim 1 wherein the reaction is run in the liquid phase.

9. The process of claim 1 which further includes contacting the 2-halo-1-alkene with carbon monoxide and an esterifying agent, in the presence of a group VIII metal catalyst and a halogen acceptor, to prepare an acrylate ester wherein the esterifying agent is an alcohol, phenol, (poly)glycol monoether or a carbonate.

10. The process of claim 9 wherein the esterifying agent is an alcohol.

11. The process of claim 9 wherein the esterifying agent is methanol, the 2-halo-1-alkene is a 2-halo-1-propene and the acrylate ester is methyl methacrylate.

12. The process of claim 9 which further includes removing the halogen acceptor which has accepted the halogen or hydrogen halide from the reactor and dissociating or decomposing to the hydrogen halide and the residual organic compound.

13. The process of claim 12 which further includes recycling the hydrogen halide for use in preparing 2-halo-1-alkenes from hydrocarbon streams.

14. A process for preparing a 2-halo-1-alkene comprising contacting a hydrocarbon stream with a hydrogen halide, in the presence of water and an effective amount of a catalyst, at a temperature between about 100° C. and about 400° C., wherein; the hydrocarbon stream comprises a 1,2-diene, a terminal acetylene or mixtures thereof, represented by the formulas $CH_2=C=CH-R$ or $CH\equiv C-CH_2-R$ wherein R is hydrogen, alkyl, cycloalkyl or aryl and may be substituted or unsubstituted; the water is present in an amount capable of maintaining the selectivity of the catalyst for the insertion of the halide on the 2 carbon of the 1,2-diene or terminal acetylene; and the catalyst comprises carbon, silica alumina, aluminosilicates, silica gel, silica, silica magnesia, silicalite, group IIIA, IIIB, IVA, IVB or V metal oxides or rare earth oxides; in the absence of mercuric halides, copper halides, aluminum halides, iron halides, zinc halides, bismuth halides, nickel halides or calcium halides.

* * * * *

UNITED STATES PATENT AND TRADEMARK OFFICE
CERTIFICATE OF CORRECTION

PATENT NO. : 4,480,121

DATED : October 30, 1984

INVENTOR(S) : Robert T. Klun; Craig B. Murchison and Dennis A. Hucul

It is certified that error appears in the above-identified patent and that said Letters Patent is hereby corrected as shown below:

Column 13, line 46, at the beginning of the line, "ng" should read -- ing --.

Column 13, line 47, at the beginning of the line, "alide" should read -- halide --.

Column 13, line 48, at the beginning of the line, "f" should read -- of --.

Column 13, line 49, at the beginning of the line, "nd" should read -- and --.

Column 13, line 50, at the beginning of the line, "omprises" should read -- comprises --.

Column 13, line 51, at the beginning of the line, "hereof" should read -- thereof --.

Column 13, line 52, at the beginning of the line, "r" should read -- or --.

Column 13, line 53, at the beginning of the line, "ycloalkyl" should read -- cycloalkyl --.

Column 13, line 54, at the beginning of the line, "uted;" should read -- tuted --.

Column 13, line 55, at the beginning of the line, "aining" should read -- taining --.

Column 13, line 56, at the beginning of the line, "he" should read -- the --.

UNITED STATES PATENT AND TRADEMARK OFFICE
CERTIFICATE OF CORRECTION

PATENT NO. : 4,480,121

DATED : October 30, 1984

INVENTOR(S) : Robert T. Klun; Craig B. Murchison and Dennis A. Hucul

It is certified that error appears in the above—identified patent and that said Letters Patent is hereby corrected as shown below:

Column 13, line 57, at the beginning of the line, "cetylene;" should read -- acetylene; --.

Column 13, line 58, at the beginning of the line, "lumina," should read -- alumina --.

(WILL APPLY TO THE GRANT ONLY).

Signed and Sealed this

Twenty-eighth Day of May 1985

[SEAL]

Attest:

DONALD J. QUIGG

Attesting Officer

Acting Commissioner of Patents and Trademarks